Figure 1A:
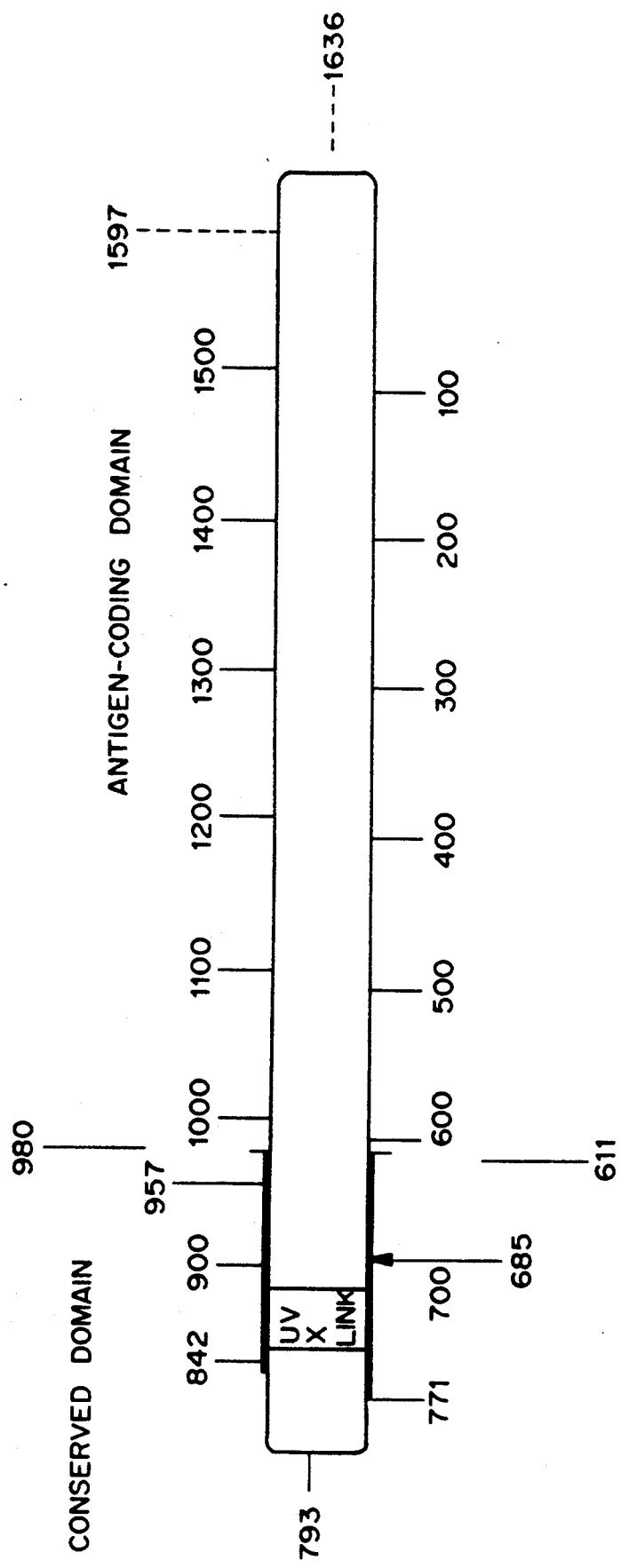

United States Patent [19]
Robertson et al.

[11] Patent Number: 5,225,337
[45] Date of Patent: Jul. 6, 1993

[54] RIBOZYME COMPOSITIONS AND METHODS FOR USE

[75] Inventors: Hugh D. Robertson; Allan R. Goldberg, both of New York, N.Y.

[73] Assignee: Innovir Laboratories, Inc., New York, N.Y.

[21] Appl. No.: 411,713

[22] Filed: Sep. 25, 1989

[51] Int. Cl.$^5$ .................. C12P 19/34; C12Q 1/68; C07H 15/12; C12N 15/00
[52] U.S. Cl. ........................ 435/91; 435/6; 435/5; 536/27; 536/23.1; 935/77; 935/78
[58] Field of Search ............ 435/6, 91, 5; 536/27; 935/77, 78

[56] References Cited

U.S. PATENT DOCUMENTS

| | | | |
|---|---|---|---|
| 4,795,700 | 1/1989 | Dervan et al. | 435/5 |
| 4,888,278 | 12/1989 | Singer et al. | 435/6 |

FOREIGN PATENT DOCUMENTS

| | | |
|---|---|---|
| 0389299 | 9/1990 | European Pat. Off. |
| PCT/US87/-03161 | 6/1988 | PCT Int'l Appl. |
| PCT/US88/-00478 | 6/1989 | PCT Int'l Appl. |
| WO8905852 | 6/1989 | PCT Int'l Appl. |
| 8905852 | 6/1989 | World Int. Prop. O. |
| 90278845/37 | 8/1990 | World Int. Prop. O. |

OTHER PUBLICATIONS

Young et al, Nature, vol. 343, Jan. 4 1990, p. 28.
Bergmann et al, in "Self-cleaving RNA as an Anti-HIV Agent:Design and Delivery to Cells", NIAID, to Jun. 21-23, 1989, p. 24.
Wu et al, Proc. Natl. Acad. Sci. USA, vol. 86, Mar. 1989, pp. 1831-1835.
Wu and Lai, Science 243, 652-654 (Feb. 3, 1989).
Wu, et al., Proc. Natl. Acad. Sci. USA 86, 1831-1835 (Mar. 1989).
Branch, et al., Science 243, 649-652 (Feb. 3, 1989).
Wu, et al., Proc. Natl. Acad. USA 86, 1831-1835 (Mar. 1989).
Waugh, et al., Science 244, 1569-1571 (Jun. 1989).
Doudna and Szostak, Nature 339, 519-522 (Jun. 1989).
Cech, Nature 339, 507-508 (Jun. 1989).
Latham and Cech, Science 245, 276-282 (Jul. 1989).
"Self-Cleaving RNA as an Anti-HIV Agent: Design and Delivery to Cells" (Development Therapeutics Branch AIDS Program, National Institute of Allergy and Infectious Diseases Jun. 21-23, 1989).
Maddox, Nature 342, 409-413 (Dec. 1989).
Young, et al., Nature 343, 28 (Jan. 1990).
Papas, Oncogenesis and AIDS (Greece, 1989).
Cech, Robert A. Welch Foundation Conferences on Chemical Research, pp. 345-355 (Nov. 4-6, 1985).
Reed, et al., Cell 30, 627-636 (1982).
Guerrier-Takada, et al., Cell 45, 177-183 (1986).
McClain, et al., Science 238, 527-528 (1987).
Altman, et al., Gene 82, 63-64 (1989).
Guerrier-Takada, et al., Science 246, 1578-1584 (1989).
Baer, et al., Nucleic Acids Research 18 (1), 97-103 (1989 or 1990).
Lee, et al., Mol. Cell. Biol. 9(6), 2536-2543 (Jun. 1989).
Pace, et al., Gene 82, 65-75 (1989).

(List continued on next page.)

Primary Examiner—Margaret Moskowitz
Assistant Examiner—Mindy B. Fleisher
Attorney, Agent, or Firm—Kilpatrick & Cody

[57] ABSTRACT

Ribozymes, sequences cleaving RNA, derived from sequences present in the hepatitis delta virus, have been engineered for greater specificity without increasing size. The specific ribozyme sequences are useful as reagents for cleaving RNA for experimental studies as well as antiviral therapies. Examples demonstrating the targeting of these sequences against HIV and Crohn's disease are described in detail. The sequences are also useful as diagnostics for the detection of hepatitis delta virus in tissue and fluid samples, as in blood banking, as well as in isolation and characterization of new viroids having ribozyme activity, using an RNA-specific hybridization method. Based on analysis of the two domain structure of the hepatitis delta virus, it is possible to construct a vector for expression of non-hepatitis delta virus proteins in mammalian cells.

9 Claims, 2 Drawing Sheets

OTHER PUBLICATIONS

Pace, et al., *J. Biol. Chem.* 265(7), 3587–3590 (1990).
Altman, *Advances in Enzymology* A. Meister, ed., vol. 62, pp. 1–36, John Wiley & Sons, 1989.
Uhlenbeck, *Nature* 328, 596–600 (1987).
Kruger, et al., *Cell* 31, 147–157 (1982).
Zaug, et al., *Nature* 301, 578–583 (1983).
Zaug, et al., *Science* 224, 574–578 (1984).
Sullivan, et al., *Cell* 42, 639–648 (1985).
Been, et al., *Cell* 47, 207–216 (1986).
Inoue, et al., *J. Mol. Biol.* 189, 143–165 (1986).
Zaug, et al., *Science* 231, 470–475 (1986).
Surratt, et al., *Molecular Biology of RNA* 79–88 (Alan R. Liss, Inc., 1989).
Bonino, et al., *J. Virology* 58(3), 945–950 (Jun. 1986).
Prody, et al., Science 231, 1577–1580 (Mar. 1986).
Wang, et al., *Nature* 323, 508–514 (Oct. 1986).
Kos; et al., *Nature* 323, 558–560 (Oct. 1986).
Chen, et al., *Proc. Natl. Acad. Sci. USA* 83, 8774–8778 (Nov. 1986).
Zaug, et al., *Nature* 324, 429–433 (Dec. 1986).
Joyce, et al., *Proc. Natl. Acad. Sci. USA* 84, 4398–4402 (Jul. 1987).
Darnell, *Scientific American.*
Taylor, et al., *J. Virology* 61(9), 2891–2895 (Sep. 1987).
Joyce and Inoue, *Nucleic Acids Res.* 15, 9825–9840 (1987).
Kay and Inoue, *Nucleic Acids Res.* 15, 1559–1577 (1987).
Pechan, et al., *Z. Naturforsch.* 42c, 1006–1008 (1987).
Kim and Cech, *Proc. Natl. Acad. Sci. USA* 84, 8788–8792 (Dec. 1987).
Hadid, *Molecular Plant Pathology* 78(5), 575–578 (1988).
Salazar, et al., *J. gen. Virol.* 69, 879–889 (1988).
Been and Cech, Science 239, 112–1416 (Mar. 1988).
Abouhaidar and Paliwal, J. gen. Virol. 69, 2369–2373 (1988).
Kuo, et al., *J. Virology* 2(6), 1855–1861 (Jun. 1988).
Negro, et al., *J. Infectious Diseases* 158(1), 151 (Jul. 1988).
Zaug, et al., *Biochemistry* 27, 8924–8931 (1988).
Haseloff & Gerlach, *Nature* 334, 585–591 (Aug. 1988).
Baltimore, *Nature* 335, 395–396 (Sep. 1988).
Cech, Jama 260(20), 3030–3034 (Nov. 1988).
Taira, et al., *Nucleic Acids Research* 17(10), 3699–3708 (1989).
Wu and Lai, *Science* 243, 652–654 (Feb. 1989).
Ruden and Gilboa, *J. Virol.* 63(2), 677–682 (Feb. 1989).

Delta +

645
CCCCACUCUCUGCAGGGUCCGCGUCCAUCCCUUACCUGAU|GGCCGGCAUGGUCCCAGCCCUUCCUCGGCCGCUGGCAACAUUCCGAGGGGACCGU
                                    685                                                    745
                                     *

Delta −

860
UCCACUCACAGGUUUGCGUCUCGCGUCCUUCUUCCCUCUUC|GGGUCGGCAUGGCCAUCUCCACCUUCCUCGACCUGGCAUCCGAAGGAGGACGCA
                                     900                                                   960
                                      *

FIGURE 1b

RIBOZYME COMPOSITIONS AND METHODS FOR USE

BACKGROUND OF THE INVENTION

This is in the general area of genetic engineering of nucleic acid sequences, especially RNA sequences, and compositions and diagnostics for use therein.

Discoveries in the basic realm of molecular biology over the past five years have led to the realization that RNA has a series of distinct capabilities and biological activities previously unsuspected. The most important of these novel RNA-level discoveries has been the finding that RNA can be an enzyme as well as an information carrier.

Since 1982, several unexpected diseases caused by RNA-based pathogenic agents have emerged. These include the lethal Acquired Immune Deficiency Syndrome (AIDS) and delta hepatitis, a particularly virulent form of fulminant hepatitis caused by a viroid-like RNA agent. These blood-borne diseases are spread at the RNA level, manifest themselves in cells of patients, and are by now present within the bloodstream of millions of individuals.

Conventional biotechnology, with its reliance on recombinant DNA methods and DNA-level intervention schemes, has been slow to provide valid approaches to combat these diseases.

As described by Thomas R. Cech, in JAMA 260(20), 3030-3034 (November 1988), certain RNA molecules can mediate their own cleavage or splicing or act as enzymes to promote reactions on substrate RNA molecules, and can therefore play an active role in directing cellular biochemistry. These findings suggest the possibility that other cellular RNAs, including the RNA components of small nuclear ribonucleoproteins, of the ribosome, and of various ribonucleoprotein enzymes, are catalysts. These activities are emerging as important contributors to the understanding of RNA processing. Splicing of introns and exons in mRNA, first described in 1977, is a major part of the RNA processing field. In the decade since RNA splicing was first described, four major categories of introns have been found, each with its own RNA splicing mechanism. As with many other biological reactions, RNA splicing requires catalysts to speed up the rate of the reaction and to ensure that splice sites are chosen accurately. In at least four systems described to date, RNA catalysts, or ribozymes, appear to be involved in RNA cleaving and splicing reactions. Ribozymes are defined as specific domains of RNA molecules which have enzymatic activity - either acting as an enzyme on other molecules, or undergoing intramolecular catalysis in reactions such as self-splicing or self-cleaving.

Ribozymes can be used as sequence-specific RNA cleavage agents in vitro, providing useful tools for biochemical studies of RNA. In studies of the rRNA precursor of *Tetrahymena thermophila*, a ciliated protozoan, Cech found splicing to be catalyzed by the folded structure of the intron itself. The observation of self-splicing was later extended to related group I introns and to the structurally distinct group II introns. In some cases the RNA catalyzed reactions also involve proteins. Splicing of group I introns takes place through two transesterification reactions, exchanges of phosphate esters that leave the total number of phosphodiester bonds unchanged. In the first transesterification step, the 5' splice site is cleaved as guanosine is added to the 5' end of the intron. In the second step, the 3' splice site is cleaved as the exons are joined. To help catalyze these reactions, the intron provides binding sites for the exogenous guanosine and for nucleotides near its own splice sites. In addition, the intron provides an active site that facilitates the reaction.

A structurally distinct group of introns found in fungal mitochondria, the group II introns, described by Michel, et al., EMBO J. 2, 33-38 (1983), also undergoes self-splicing. As with the group I introns, splicing occurs through two transesterification reactions, the first involving the 5' splice site and the second the 3' splice site. In contrast to the group I intron mechanism, the attacking group (nucleophile) for the first transesterification is the 2'-hydroxyl group of an adenosine located within the intron. The product of transesterification is a branched RNA called a lariat. Nuclear mRNA introns in all eukaryotes studied appear to undergo splicing in the same manner as the group II introns.

An enzyme can be defined as a molecule that greatly accelerates the rate of a chemical reaction, with great specificity for its substrates and for the type of reaction it facilitates, which is not consumed in each reaction, so that one enzyme molecule can interact with numerous substrate molecules. Self-splicing RNA of the type present in group I and group II introns is not a true enzyme since it is altered by the reaction. As described by Cech, et al., in PCT/US87/03161, however, deletion or substitution of some of the nucleotides can be used to convert the self-splicing group I intron into an enzyme having a specificity for a sequence of four nucleotides. Removal of the first 19 nucleotides of the Tetrahymena rRNA intron produces a form called the L-19 intervening sequence RNA. This molecule no longer contains sites for intramolecular reactions but can mediate reactions on added substrate RNAs without itself undergoing any net change in the process. The first activity described for this RNA enzyme was the assembly of short chains of RNA into longer chains, i.e., an RNA polymerization activity, as reported by Zaug, et al., Science 231, 470-475 (1986).

A second activity of the RNA enzyme derived from the Tetrahymena intervening sequence is that of a sequence-specific endoribonuclease, described by Zaug, et al., Nature 324, 429-433 (1986). This RNA enzyme is able to cleave other RNA molecules that are single stranded with considerably more sequence specificity than any known protein ribonuclease (RNase). Recognition is provided by the sequence of nucleotides preceding the cleavage site, and cleavage is accomplished by guanosine addition. Site-specific mutagenesis of the enzyme active site (the sequence 5'-GGAGGG-3') alters the cleavage specificity in a predictable manner so that it has been possible to synthesize endoribonucleases to cut at a variety of sequences.

Two other major categories of RNA catalysis have been investigated, the first including examples from several different organisms of RNase P, a ribonucleoprotein enzyme that makes a specific cleavage in tRNA precursors; and the second including a variety of self-replicating RNAs that infect plants and animals, the viroid-like pathogens (or VLPs). As reported by Guerrier-Takada, et al., Cell 35, 849-857 (1983), the reaction involving the RNase P is similar to that catalyzed by the group I and group II introns, with the difference that the attacking entity is water instead of a ribose hydroxyl group.

Several of the VLP RNAs that infect plants, including one viroid (a small circular RNA that is infectious by itself) and several virusoids and satellite RNAs (circular and linear RNAs, respectively, that are encapsulated by the coat proteins of certain plant RNA viruses), undergo efficient site-specific self-cleavage in vitro, described by Prody, et al., Science 231, 1577-1580 (1986), and Hutchins, et al., Nucleic Acids Res. 14, 3627-3640 (1986). These RNAs share a small structural domain, consisting of only about 30 nucleotides, called a "hammerhead". During infection, self-cleavage is thought to be responsible for conversion of linear RNA multimers produced by rolling circle replication into unit-size progeny. The requirements for cleavage, which leaves a cyclic phosphate at the 3' end of the upstream cleavage product, are described by Uhlenbeck, Nature 328, 596-600 (1987) and Forster, et al., Cell 50, 9-16 (1987).

Hepatitis B virus, having a small, circular, partially double-stranded DNA genome, causes viral hepatitis and hepatocellular carcinoma in man. Hepatitis delta virus, containing a small, circular RNA, is a satellite virus of the hepatitis B virus. Superinfection of carriers of hepatitis B virus with hepatitis delta virus causes a fulminating hepatitis frequently leading to death. The hepatitis delta virus RNA is circular and has a structure characterized by intramolecular base pairing, similar to that of viroids and virusoids that infect plants, as demonstrated by Wang, et al., Nature 323, 508-514 (1986), and Chem, et al., Proc.Natl.Acad.Sci. USA 83, 8774-8778 (1986). Sharmeen, et al, demonstrated in J. Virol. 62, 2674-2679 (1988), that hepatitis delta virus RNA can undergo a type of self-cleavage in vitro. The cleavage products have 2',3'-cyclic phosphate and 5'-hydroxyl termini. The sequences and structures responsible for self-cleavage were not delineated but were predicted to be different from the hammerhead motif found in virusoids.

In a related finding Branch, et al., in Science 243, 649-652 (Feb. 3, 1989), demonstrated the existence of a novel structural element in HDV genomic RNA which lies within the highly conserved domain of HDV RNA and may be related to the local tertiary structure previously mapped to the central conserved region of the plant viroid genome. These authors also pointed out the close proximity of this structural element to the site of delta RNA self-cleavage. At the same time, Wu and Lai reported in Science 243, 652-655 (Feb. 3, 1989), that a 148 nucleotide subfragment of hepatitis delta virus RNA reversibly undergoes cleavage and ligation. The direction of the reaction is determined by the presence or absence of $Mg^{2+}$ ions, with the presence of $Mg^{2+}$ favoring the cleavage reaction. Ligation requires specific conformation of the RNA molecules involved and occurs only between two cleaved RNA fragments that are held together by hydrogen bonds. Ligation occurs on removal of $Mg^{2+}$ by EDTA. In March 1989, Wu, et al., reported in Proc. Natl. Acad. Sci. USA 86, 1831-1835, that cleavage can be accomplished with subfragments of the hepatitis delta virus 1.7 kb genome as short as 133 nucleotides in the presence of at least 500 $\mu M$ $Mg^{2+}$ or $Ca^{2+}$, much lower concentrations than are required for cleavage by hammerheads, at a pH from 5.0 to 9.1, generating a 5' fragment with a terminal uridyl 2',3'-cyclic monophosphate residue and a 3+ fragment with a guanosyl residue with a 5'-hydroxyl group.

There have been a number of suggestions in the literature that ribozymes may have utility as reagents or as therapeutic agents, although little has been accomplished in implementing this goal. The Tetrahymena sequence, as well as the subsequently discovered sequence in yeast, is not a true enzyme since it is not regenerated in the process but instead acts in a stoichiometric ratio. Although it is possible to engineer fragments of this sequence which have enzymatic activity and are able to cleave and ligate RNA, a disadvantage to these fragments is that they are very large (requiring more than 200 residues of the original 415 nucleotide sequence) and of limited specificity. It has been suggested that the RNA subunit of E.coli RNAse P (MI RNA) which cleaves extra RNA sequences from the 5' ends of tRNA precursors, to create mature tRNA molecules can be engineered so that its substrate-recognition region is twenty nucleotides or less.

The viroid-like pathogens, VLPs, can be divided into two classes: Class I, free living viroids; and Class II, including virusoids and satellite viroids (RNA molecules which require a helper virus to replicate). The hepatitis delta virus is a Class II VLP by this definition. VLPs have two types of ribozymes. The first of these types, the "hammerhead", is being commercially exploited by Haseloff and Gerlach of CSIRO, Canberra, Australia. Uhlenbeck, Nature (1987), first developed these small (down to 18 nucleotides), and relatively specific ribozyme sequences from plant viroids such as avocado sunblotch viroid and the satellite RNAs of tobacco ringspot virus and lucerne transient streak virus. In their present forms, the Tetrahymena ribozymes have four-base recognition sequences and the hammerhead ribozymes have approximately 12-base recognition sequences. Any four-base sequence appears several times, on average, in an RNA the size of a typical mRNA, in contrast to 12-base sequences, allowing these ribozymes to be used in a complementary fashion to cleave RNA.

As far is known, none of these ribozymes has been used so far for anything other than as laboratory reagents for cleaving and splicing of RNA with somewhat limited specificity. In addition to the limitations of size, the relatively broad specificity of the ribozymes has made it difficult to target only the RNA to be cleaved, especially without doing any damage to the host RNA. No non-plant viroids besides hepatitis delta virus have been definitively characterized at this time. Thus, the key knowledge for harnessing any class of ribozyme, including the delta ribozyme, i.e., knowledge of its detailed, primary, secondary, and tertiary structure resulting in understanding of its mechanism, has yet to be achieved.

It is therefore an object of the present invention to provide methods and compositions for specifically cleaving targeted RNA sequences.

It is a further object of the present invention to provide methods and compositions for specifically cleaving RNA, both in vitro and in vivo, for the treatment of disease conditions which involve RNA expression, such as AIDS.

It is also an object of the present invention to provide methods and compositions for detecting, and treating, the viroid-like agent causing delta hepatitis, as well as additional viroid-like agents, including the agent responsible for Crohn's disease.

It is yet another object of the present invention to provide methods and compositions for constructing tissue specific expression vectors and vaccines based on the delta hepatitis viroid.

SUMMARY OF THE INVENTION

Ribozymes which cleave RNA are derived from a specific domain present in the hepatitis delta virus (HDV) RNA, and have been engineered for greater specificity without significantly increasing size. The delta ribozyme domain is composed of specific elements of primary, secondary, and tertiary structure and is useful as a reagent for cleaving RNA for experimental studies as well as antiviral therapies. Examples demonstrate the targeting of these sequences against HIV, using 10 to 15 base secondary structures and tertiary structural elements in the vicinity of the ribozyme predicted by the two domain model of hepatitis delta RNA. The conserved regions of delta RNA containing these elements are composed of sequences which are also useful as diagnostics for the detection of hepatitis delta virus in tissue and fluid samples, as in blood banking, as well as in isolation and characterization of VLPs, using RNA specific hybridization methods. The novel RNAs identified by hybridization will then be characterized as VLPs if they include replicating non-host RNA sequences having tertiary structure which is sensitive to ultraviolet crosslinking and ribozyme (RNA cleaving) activity, and conserved sequences among different strains of the same viroid are found.

BRIEF DESCRIPTION OF THE DRAWINGS

FIG. 1A is a schematic of the delta hepatitis genome. Residue numbers are based on Wang, et al., Nature 323, 508–514 (1986). The heavier lines in the Conserved Domain represent sequences of greatest invariance in strains so far characterized. The area marked "UV" defines the local tertiary structure present in this region. The upward arrow in the lower left of the drawing represents the exact cleavage between residues 685–686 which is catalyzed by the delta ribozyme. The delta protein, or antigen, is encoded by residues 957–1597 of the Antigen-coding Domain.

FIG. 1B the sequences containing delta ribozyme activity. "Delta+" shows the sequence of delta residues 645–745, which includes the cleavage site (shown by a "*" at residues 685–686); and the area of local tertiary structure, in residues 703–735. "Delta-" shows the corresponding region of the delta antigenomic strand, which contains a ribozyme site at residue 900.

DETAILED DESCRIPTION OF THE INVENTION

There are several principal applications of sequences and structures derived from hepatitis delta RNA and related VLPs having ribozyme activity and secondary and tertiary structure: as agents of RNA cleavage, as prophylactic and therapeutic agents, and in expression systems.

Delta acts like a viroid and yet carries a sequence encoding an unrelated protein, as shown in FIG. 1A. Clustering of viroid activities, including self-cleavage of a rolling circle of RNA, and ligase activity, allow one to jettison the protein encoding sequence and substitute a second protein encoding sequence. The viroid-like region has a variable and conserved region about 350 to 400 bases. The protein coding region is about 1200 bases. The primary ribozyme activity is in the viroid-like region at about bases 645 to 745, as shown in FIG. 1B, and cleaves the bond between bases 685 and 686. The complementary antigenomic strand of delta RNA also has ribozyme activity centering around residue 900. The subdomain in the viroid-like region having local tertiary structure involves bases 703 to 735. The local tertiary structure causes the subdomain between bases 703 and 735 to associate with bases 856 to 876, which is believed to regulate the ribozyme by causing structural transitions or stabilizing structures needed for cleavage. The sequence for bases 856 to 876 is: AUG CCC AGG UCG GAC CGC GAG.

Since the work which was published by Branch, et al., Science (1989) was completed, significant further progress has been made in bringing together various observations about delta RNA in a way which now allows concrete applications in the areas of viral therapy and diagnosis, as well as the creation of RNA based expression vectors. The insights which have done this are the experimental result that the viroid-like features of delta RNA are clustered in a single, small subgenomic domain and, that, in particular, the delta ribozyme is embedded in characteristic areas of primary, secondary, and tertiary structure. By direct comparison with data from several ribozyme classes it was possible to predict and then carry out experiments which show that all three levels of structure are vital to the ribozyme's function. Therefore, knowledge of the two domain structure of delta RNA is directly required to plan and synthesize the modified ribozyme sequences targeted toward specific pathogenic viral RNAs. Furthermore, the two domain model, by showing where the conserved regions of the delta RNA genome are located and why they are likely to be conserved in other strains of delta and other VLPs as well, is vital to the design of successful diagnostics. This conclusion follows from the fact that knowledge of sequence, base-paired structure, and local tertiary structure all influence the efficiency with which a hybridization probe to the conserved delta sequence will bind and thus correctly identify delta RNA with high efficiency as distinct from the cellular RNA background. Without the two domain model, it would not be possible to design and synthesize the right probes for identification of delta RNA and other VLPS. The fact that delta RNA's domains are separated by regions which undergo RNA cleavage during replication (i.e., by sites containing ribozymes) has pointed the way to the expression vector system by allowing use of modified delta sequences which still contain everything needed for replication but within which the protein-coding sequence for the delta antigen is replaced by RNA encoding different proteins.

1. Reagents

DNA restriction endonucleases are invaluable reagents for the molecular biologist. Patterns of restriction fragment sizes are used to establish sequence relationships between DNA molecules, and large DNAs can be cleaved to give fragments of sizes useful for genetic engineering, sequencing, and studying protein binding. Ribozymes, on the other hand, cleave RNA with considerably more sequence specificity.

Small, specific ribozymes can be prepared from HDV using the catalytic sequence flanked with nucleotide sequences complementary to the sequence targeted for cleavage. In addition, the conserved, viroid-like domain of hepatitis delta RNA contains a higher order structure having RNA processing function. It has been shown that knowledge of all three elements primary sequence, secondary structure as defined by Watson-Crick base pairing, and the local tertiary structure element - is required for use of the delta ribozyme. Using transcripts from a series of DNA constructs spanning a region of this domain which contains a characteristic element of local tertiary structure (defined by UV-induced RNA:RNA crosslinking) and elements required for RNA cleavage reactions, the bases involved in the covalent, UV-induced crosslink were identified. Since this pre-existing structure within delta RNA defines characteristic non-Watson:Crick elements likely to be important to processing, replication and other functions of this viroid-like pathogen, mutant and wild-type RNA domains containing this structural element can continue to be compared to ascertain its role in biological function and to determine the most desirable modifications of the structure. Residues 650 to 730 of the delta genome participate in these reactions and delineate the key region. These residues are shown in FIG. 1B.

These sequences have applications as laboratory reagents, in a similar fashion to restriction enzymes, and as therapeutic agents, for cleavage and inactivation of specific bacterial and viral sequences in vivo. A present limitation to the in vivo use is the ability to get the modified sequence into the cell, although it has been demonstrated that HDV can infect hepatocytes in the absence of the Hepatitis B virus (HBV).

2. Diagnostics

The HDV sequences can be used alone or in combination with antibodies to HDV antigen to provide screening tests for HDV which are more accurate and more sensitive than present methods. Furthermore, the same techniques for detection of sequences and/or antigen can be used for detection of HBV.

Hepatitis delta has been seen generally in the presence of hepatitis B virus (HBV). Coincident infection by delta and HBV frequently results in severe and often fatal fulminant hepatitis. Recently collected data indicate that in certain groups, such as intravenous drug abusers, from 40–70% are infected with delta, as well as HBV. In the U.S. there appears to be a parallel increase in levels of delta agent infection and HIV infection. Currently each unit of blood that is stored for potential transfusion is tested for the presence of HIV and HBV. Although a test for delta is needed, the current research laboratory antibody test for delta is not reliable enough to be used by blood banks. Such centers rely on HBV tests to indicate the possible presence of delta, but recent data suggest not only that delta can replicate in the absence of HBV, but also that no combination of HBV tests can substitute for direct detection of delta itself. Furthermore, certain HBV tests routinely used give a high percentage of false positives, wasting tens of thousands of units of blood annually. According to preliminary reports, less than half of the cases identified under the loose term "non-A, non-B hepatitis" show evidence of a new agent, now called hepatitis C virus (HCV). Many of the remainder could harbor the hepatitis delta agent as well.

The hepatitis delta agent has as its principal antigenic protein the HBV surface antigen. Delta agent infection also stimulates production of an additional new antigen, antibodies to which can be detected in some but not all cases of delta infection. An assay for delta which uses an antibody to HBV surface antigen for detection of delta cannot reliably distinguish between hepatitis B and delta. The only reliable way to track this unconventional RNA pathogen is by direct detection of its genomic RNA. Using a series of RNA-level synthesis and labeling techniques, specific probes to critical regions of the RNA of the delta agent can be constructed using $^{125}$I-labeling and RNA:RNA hybridization techniques.

The probe for the delta RNA should be efficient and based on direct nucleic acid hybridization techniques in which Watson:Crick base pairing of perfectly complementary sequences is the key to specificity. For detection of delta, it is preferred to use $^{125}$I-labeled nucleic acid probes in a standard radioimmunoassay coupled with conventional "dot-blot" or "slot-blot" hybridization technology. RNA polymerase from a bacterial virus such as SP6 or T7 is commercially available and is being used in the synthesis of a whole variety of specific RNA's from specific DNA templates. Accordingly, any sequence that has been cloned by conventional genetic engineering technology can be moved as an insert into another DNA which contains the promoter sequence for one of these two RNA polymerases, and the combined DNA copied to give the desired RNA in milligram quantities in the test tube. Delta RNA clones are available and can be copied using this technique. Further, the sequence of the delta genomic RNA has been published by Wang, et al. Nature (1986). The desired oligonucleotide can be made synthetically and copied with T7 RNA polymerase to produce large amounts of a desired RNA sequence with no cloning, by attachment of a pre-synthesized promoter segment for the RNA polymerase to a single strand of synthetic DNA containing 30–40 bases of the desired sequence.

The sequences can be radiolabelled with $^{125}$I-labeled CTP, which is now commercially available from England Nuclear, Corp., Waltham, Mass. This $^{125}$I-CTP is specifically incorporated into VLP-specific probes and transcripts. RNA copies of the appropriate polarity are made in the presence of $^{125}$I-labeled CTP and other standard components. The resulting RNA is phenol extracted, chromatographed over cellulose CF-11 to remove unincorporated label, and then tested by fingerprinting and other techniques to confirm its sequence. Hybridization tests are carried out subsequently on filters dotted with serum samples or extracts thereof. Nonradioactive detection can also be used.

Two considerations are critical for developing a routine test: (1) ease of production of the samples; and (2) reliability of the assay. Both simple and complex procedures for serum—the first biological component to be tested for the presence of delta agent—are being tested to determine the most facile approach. In one case, the test calls for mixing a denaturant such as formaldehyde with diluted serum samples (e.g., 50 microliters diluted to a total volume of 0.5 ml), concentrating the RNA and other materials, and spotting directly onto filters. More complex procedures up to and including phenol extraction are being tested in parallel to determine efficiency. After drying in a vacuum oven, filters are hybridized with $^{125}$I-labeled specific RNA probes (and controls complementary to RNA's other than the delta agent) and subjected to autoradiography using light intensifying screens. $^{125}$I is the ideal radioisotope for this latter approach, with its comparatively long half life (60 days) combined with its abundance of secondary beta decay particles.

Several probes complementary to various regions of the delta agent genome can be mixed together in order to maximize detection efficiency and to guard against rapid change in the delta genome, as has been observed for HIV, in which many regions rapidly drift to new sequences. Separate probes can be used for the conserved region of the delta genome, which has been identified by comparative sequence analysis. The conserved region accounts for about 20% of this VLP's RNA genome.

Techniques for the detection of additional viroid-like RNA's of human and animal cells in addition to the delta agent are based on evidence of circular RNA's and multimeric copies of a monomeric entity. These two properties together have so far proven to be reliably diagnostic for viroids and viroid-like agents. The circular RNAs are detected with two-dimensional polyacrylamide gel electrophoretic run under partially denaturing conditions. In this assay, circular RNA's migrate far from all other forms of RNA, and can thus not only be detected but also purified. A search, in these same samples, for sets of multimeric RNA's (which need not be circular) can be undertaken using the detected RNA circles, or selected sequences copied therefrom, as probes. Finally, hybridization probes for the conserved region of delta are being harnessed in screens for VLPs in other tissues.

Although described herein with specific reference to diagnostics, expression systems and therapeutics derived from engineered hepatitis delta RNA, it is anticipated that similarly engineered RNA sequences and structures can be derived from the VLPs isolated from other sources, using methods such as those described above.

Examples of the kind of diseases which should be screened include those in which "slow viruses" have been implicated, for which the failure of the "prion" hypothesis to explain infectivity has greatly accelerated the search for a small RNA associated with these diseases (e.g., scrapie and Creutzfeld-Jacob syndrome) in a number of laboratories. The HDV sequences can also be used to screen for other viroid-like agents, such as the viroids postulated to be a causative agent in Crohn's disease, multiple sclerosis, and rheumatoid arthritis. The sequences are labelled and used in specific hybridization assays to screen for RNA sequences showing conserved regions, UV crosslinking and ribozyme activity. These assays may also be developed to select candidate RNA sequences or molecules that could then be screened for viroid-like properties: sequence comparison, UV crosslinking, two dimensional polyacrylamide gel electrophoresis for determination of circular geometry, and ribozyme activity.

Crohn's disease is a widespread human intestinal ailment which appears to be associated with a VLP. Crohn's disease is a chronic, inflammatory, painful human affliction of unknown etiology, which results in the slow destruction of the alimentary tract, that may appear at any site from mouth to anus, but that characteristically involves the distal small bowel and colon. It is chiefly a disease of younger people, with peak incidence of onset occurring in teenagers. Nearly 60% of all cases begin between ages ten to twenty-five. The world-wide prevalence of the disease is 60 per 100,000 population, and the annual incidence figure is 6.1 per 100,000 individuals. For comparison, the current annual incidence rate for AIDS is 13.7 cases per 100,000 population. A Crohn's diagnostic test utilizable in the physician's office, clinic, and hospital is estimated to have an annual market potential of 20 million tests in the U.S. The only available diagnostic for Crohn's involves conventional microscopic examination of bowel and colon tissue. The current diagnostic is unable to anticipate the onset of Crohn's, but rather only the existence of the established disease. This test is time and labor intensive.

No definitive association with either bacteria or viruses has been established for Crohn's disease. However, recent data indicate that three unique circular RNA species, whose length range from 300 to 800 nucleotides, are present in RNA preparations from granulomatous bowel tissue from several patients diagnosed with Crohn's disease. A clinically useful hybridization probe directed at these Crohn's-specific RNA species will enable a surgeon to biopsy the colon of a patient with Crohn's disease prior to surgery to determine the location of the infectious agent by in situ hybridization and thereby allow precise surgical extirpation of the infected tissue. Seventy five percent (75%) of patients with the disease will eventually require an operation and the capability to locate precisely the diseased tissue is needed. Currently, surgeons decide which tissue to excise on the basis of macroscopic observation. This method is clearly inefficient since recurrence rates are greater than 31% in 5 years and 60% in 10 years.

Additional diseases that are currently believed to have a viral etiologic agent, but which lack a proven characterized pathogen, will be initially screened for viroid-like RNA; these include arthritis and multiple sclerosis.

3. Therapeutics a. Ribozyme-based therapeutics

Any cellular gene product expressed as RNA, including proteins encoded by mRNA and structural RNAs themselves, can be targeted for specific cleavage and inactivation by ribozymes engineered to include appropriate regions of sequence and structure, especially HDV ribozyme. The cellular gene product could be a modified product of an oncogene, such as the ras gene product, where the product is not a normal cell component; a viral protein, such as one encoded by an essential gene for HIV replication; or a bacterial protein.

Specific delivery into the cell should be possible to achieve using retroviral technology. Defective retroviral vectors, which incorporate their own RNA sequence in the form of DNA into the host chromosome, will be engineered to incorporate the modified ribozyme sequence into the host, where copies will be made and released into the cytoplasm to interact with the target nucleotide sequences.

b. Non-ribozyme based vaccines.

A second major therapeutic approach involving delta RNA is based on evidence that pre-existing infection with one strain of HDV limits subsequent infection by other strains. HDV can be attenuated for use as a "vaccine" against subsequent infection with HDV. The mechanism of this "cross protection" by delta strains is not known. In one form, the conserved regions of the delta RNA are linked to a sequence encoding a protein other than the delta antigen, or to a sequence encoding a modified delta antigen, in the event that the delta antigen contributes to, or is the cause of the severity of HDV infection, and the patient is infected with the non-pathogenic modified HDV. In another form, base changes in the conserved sequence of delta are made which lead to different affinities for a host component in wild-type delta versus the modified delta, and therefore is non-pathogenic. The patient is infected with the modified delta and thereby protected against infection by virulent delta strains.

The RNA genome of the hepatitis delta virus is divided into two domains of unequal size: a viroid-like domain, containing most functions for replication; and a protein-coding domain, encoding the delta antigen. One of the most important functions of the viroid-like domain, that of RNA processing, is autocatalytic in nature, such that RNA-catalyzed cleavage and ligation take place. The ability of a covalently closed, circular single-stranded RNA molecule to replicate at early times may have been critically dependent upon its ability to undergo self-catalyzed cleavage and ligation steps. Furthermore, the development of such a circular, single-stranded RNA molecule with two domains, such as the genome of the delta agent, may reflect further evidence that such abilities to cleave and ligate RNA were critical in its early evolution. That RNA molecules capable of self-catalyzed ligation may have picked up coding segments, such as that encoding the delta antigen, and that such processes may continue to operate, can be used to construct new systems allowing protection of infected cells using the ribozyme domain of the molecule in combination with a sequence encoding a non-delta protein. In other words, this second or "vaccine" approach to delta hepatitis and other VLP-linked diseases grows naturally from a knowledge of the two domains and the way in which delta RNA evolved into its present form. Further, the ribozyme domain of the delta virus can be combined with a protein which is desirable and the combination used for expression of the non-delta protein in infected cells.

Based on analysis of the two domain structure of the hepatitis delta virus, it is possible to construct a liver-specific vector for expression of non-hepatitis delta virus proteins in mammalian cells. Using the methods for isolation of other viroids, it should be possible to isolate other tissue-specific viroids for construction of similar tissue-specific viroid-based expression systems. These viroid-derived sequences can also be used as "vaccines" to prevent co-infection by more virulent strains of the viroid.

4. Expression Systems

Because HDV contains a protein encoding sequence, infects cells even in the absence of HBV, and can be replicated many thousands of times in a single cell, it forms the basis for an improved expression system for proteins in eukaryotic cells, especially hepatocytes, either in cell culture or in vivo, for example, to replace missing enzymes or other proteins such as insulin. In the preferred form, a sequence encoding the protein to be expressed is inserted into HDV in place of the sequence encoding the HDV antigen. The two domain model of delta RNA predicts that the viroid-like domain—preserved intact during these manipulations—allows continued replication but now with expression of the new protein encoded in the altered delta RNA.

Assuming that the methodology used to isolate HDV, or probes prepared from HDV, is useful in isolating viroids specific to other cell types, such as intestinal cells, as may be the case of a viroid-like agent in Crohn's disease, it should be possible to make expression systems specific for cell types other than hepatocytes, and to explore systems for the uptake of delta and these other viroid-like agents which would be applicable to all cells.

EXAMPLE 1

Isolation and characterization of the two domains of the Hepatitis delta virus and production of modified ribozyme sequences from the isolated conserved region.

The Hepatitis Delta Virus (HDV), previously referred to as the delta agent, is a mammalian pathogen bearing a strong similarity to the viroids and related satellite RNAs of plants. Like viroid genomes, the genome of HDV is a covalently closed RNA circle and is smaller than the genome of any conventional virus. Furthermore, unlike defective interfering particles, HDV RNA has no significant sequence homology with its helper virus, hepatitis B virus, and thus more closely resembles many plant satellite RNAs. In addition, multimeric forms of both the genomic and antigenomic strands have been reported in tissues replicating HDV. As in the rolling circle replication pathway first proposed for the small infectious RNAs of plants, these multimeric HDV precursor RNAs are thought to be cleaved and ligated to yield progeny circles Finally, a rodlike secondary structure has been drawn for HDV RNA, which is very much like the one that has emerged from detailed studies of plant viroid sequence and structure. Evidence now places an ultraviolet (UV)-sensitive site within transcripts of HDV RNA which provide experimental support for the proposed secondary structure of HDV RNA and reveal tertiary structural elements as well. A similar UV-sensitive site was mapped in potato spindle tuber viroid RNA and is being used to define the structure of the viroid central conserved region. The results with UV-induced crosslinking of HDV RNA constitute one feature of several that have helped to identify the viroid-like domain in the genomic RNA of this pathogenic agent.

To obtain material for structural analysis, RNA of the genomic polarity was transcribed in vitro from a full-length cDNA clone of HDV RNA and several partial clones. For initial screening, transcripts of these cDNA clones were exposed to UV light for 90 s, under conditions previously used to crosslink UV-sensitive tertiary elements in viroids and eukaryotic 5S ribosomal RNA (rRNA). Both irradiated and control delta transcripts were digested at 37° C. with ribonuclease T1 (RNase T1). The products were fractionated by gel electrophoresis to seek a UV-dependent band that might contain a photo-induced crosslink, which would signal the presence of a novel tertiary structure in the genomic strand of HDV RNA. A prominent band was present in UV-irradiated samples of both genome-length RNA and smaller partial transcripts. This RNase T1 digestion method permits even large RNAs to be analyzed. Because their shorter length would allow two-dimensional gel electrophoresis to be used as a purification step for intact cross-linked forms, transcripts of the two partial clones mentioned above were used for further investigations.

Oligonucleotide mapping by standard techniques demonstrates that only two segments of the transcripts could give rise to the oligonucleotides present in the fingerprint of the crosslink-specific RNase T1-resistant region of HDV genomic sequence. The released oligonucleotides define two noncontiguous segments of the delta genome. One segment contains residues 703 to 735, and the other, bases 856 to 876. From the portion of the secondary structure map containing the RNase T1-resistant region, it is evident that the RNase T1 partial digestion product contained a minimum of 54 bases, including 16 G residues.

The regions so defined can be seen from FIG. 1A to be in the immediate vicinity of the delta self-cleavage site, which occurs at residue 685. Residues 703-735, which are adjacent to residue 685, are present in all subgenomic fragments which show ribozyme activity that have been studied so far. That these same residues participate in a UV-sensitive region of local tertiary structure must be taken into account in explaining the nature of their ribozyme activity.

It is likely that the two bases that become joined by the UV-induced crosslink lie within an element of local tertiary structure containing non-Watson-Crick bonds. The UV-sensitive sites in potato spindle tuber viroid and eukaryotic 5S rRNA occur in similar regions, which are devoid of conventional bonds and are flanked by helical regions. In these molecules, the unusual spatial orientation of two bases within the structural element causes them to become crosslinked by UV treatment. UV crosslinking experiments have provided essential information concerning the structure of several other types of RNA; delta RNA is part of the group that can now be studied by this powerful technique. Tertiary bonds in transfer RNA help to establish its three-dimensional structure. Similarly, non-Watson-Crick bonds may be important in other kinds of RNA. In particular, RNAs whose functions extend beyond the encoding of genetic information may require interactions that cannot be carried out solely by Watson-Crick base pairing.

In particular, the enzymatic function of the delta ribozyme will depend not only on sequence (primary structure) and base pairing (secondary structure) in the vicinity of the cleavage activity, but upon the local tertiary structural element as well. Analysis of its structure reveals folding properties involving bases 703-735 which will be needed in the applications of the delta ribozyme for the therapeutic purposes described herein. Furthermore, this is likely to be a general requirement of all ribozyme-based systems. However, the delta ribozyme system is the only one for which the tertiary interactions have been defined, by the UV-crosslinking work, to date.

In summary, although the four reported sequences of HDV (representing two strains) differ by about 10% overall, two stretches extending over 295 bases and containing the cross-linking site have but a single base change, defining a domain about the size of conventional viroids [which range from about 250 to 400 bases]. The UV-sensitive site in potato spindle tuber viroid lies in the most highly conserved region of the plant viroid genome, in a portion of the molecule thought to be involved in replication. The proximity of the UV-sensitive element in HDV RNA to self-cleavage sites in the genomic and the anti-genomic strands, and the location of these components within the only extensive region of conserved delta sequence, suggested that the delta agent is composed of two parts. In this model, structures required for a number of replication functions cluster into a viroid-like domain, which makes up the left quarter of the genome. Of the remaining three-quarters, almost half is dedicated to encoding the delta antigen, and much of the other half may serve to stabilize this coding region, in addition to specifying any functions of its own.

EXAMPLE 2

Preparation of Hepatitis Delta Diagnostics

The use of the sequence of the conserved hepatitis delta region will give a reliable and reproducible ability to detect delta agent RNA in patients carrying a variety of strains of the disease. The remainder of the delta RNA, in common with the HIV virus causing AIDS, undergoes a rapid and irreversible divergence of sequence, so that tests aimed at detecting sequences in this second domain of the delta RNA would rapidly become unreliable. However, upon detection through probes for the conserved, viroid-like region, delta agent strains can then be further characterized by probes designed to detect alternative sequences in this "variable" region of the delta genomic RNA.

So far, sequence analysis has revealed up to 20% variation in this region, which may be related to the severity of disease reported in some outbreaks of delta hepatitis, and the relative mildness of others. Furthermore, by analogy to the plant viroids, there are likely to be limited portions of the conserved domain of the delta agent RNA which are maintained even in distantly related VLPs, such as that thought to be responsible for Crohn's disease. This insight forms the basis for an approach to screening a variety of tissues for potential VLPs using hybridization probes from conserved delta regions, and conserved regions of other VLPs as they are identified.

Example 3

Preparation of Ribozyme-Based Therapeutics: for HTLv-1 & HIV

The ability to introduce specifically engineered nucleic acid sequences, as a means of targeted therapy, into hematopoietic cells of patients suffering from virus-induced disease of those cells, such as AIDS, has overwhelming potential. The most efficacious methodology presently available for the introduction of specific genetic sequences into human cells involves the use of RNA-containing retroviruses which serve as vehicles or vectors for high efficiency gene transfer into human cells.

The two-domain structure of VLPs, defines the location and sequence of the ribozyme, the intrinsic RNA-based RNA cutting activity embedded within the genetic material of these infectious agents. The nucleotide sequence of a ribozyme from a human VLP incorporated into a retroviral vector results in the creation of a unique therapeutic agent for inactivation of pathogenic RNA sequences.

The specificity of the agent results from the addition of flanking complementary sequences that surround the ribozyme, thereby directing the ribozyme to a specific location for cleavage within the targeted RNA. The complementary sequences allow the ribozyme to be closely juxtaposed to the target RNA which it can then cut and inactivate. Furthermore, appropriate regions of local tertiary structure can be engineered to ensure maximum cleavage efficiency. The range of targets is dependent only on knowledge of the target sequences and on how the delta ribozyme operates. Once the target sequence is identified, appropriate sequences on either side of it are chosen of about 15 nucleotides in length, and exact complements to these region, inserted next to the delta ribozyme area, are constructed using standard Watson:Crick base pairing rules and genetic engineering. Furthermore, using knowledge of the tertiary structure formed between bases 703-735 of the delta ribozyme region and the closely placed bases 856-876, the surrounding structure of the synthetic delta ribozyme being constructed can be adapted to ensure appropriate tertiary interactions with the analogous region of the target sequence. In this way, the structural integrity of the ribozyme:substrate complex formed at the site of cleavage will be maximized and the rate of cleavage adjusted to the highest level.

This ribozyme approach to anti-viral therapy has major advantages in efficiency and specificity over all other approaches, particularly in conjunction with an efficient gene transfer system for therapy of viral diseases of hematopoietic cells.

Ribozyme-based therapy can also be used as a means of preventing the spread of HIV-1 and/or providing an HIV-1 resistant population of T-cells that will be able to confer immune function to infected individuals. Patients who have been recently diagnosed to have antibodies to HIV-1, but who do not yet show AIDS symptomatology, will most likely be the best candidates for therapy. This procedure will necessitate removal of some of the patient's bone marrow stem cells and subsequent partial cytoablation. The removed cells will be treated in the laboratory with the unique ribozyme-based therapeutic and then will be restored to the same individual. The treated cells will develop in the patient into mature hematopoietic cells, including T-cells. These T-cells will have normal immune function and, most importantly, will be intracellularly immunized to prevent their destruction by any HIV-1 still present in the patient. Thus, this unique therapy will provide the means for the patient to stave off opportunistic infections, the cause of death in HIV-1 infected individuals.

Bone marrow stem cells and hematopoietic cells are relatively easily removed and replaced and provide a self-regenerating population of cells for the propagation of transferred genes. As described above, HIV-1 and HTLV-1 should be amenable to these approaches. In the longer term, it is anticipated that the use of ribozyme-based therapeutics will allow the selective inactivation of other unwanted genes in cells, such as activated oncogenes, involved in the causation and maintenance of cancer cells.

Infectious diseases caused by retroviruses that have integrated into the chromosomes of infected cells represent unique challenges to the imagination and ingenuity of bio-medical scientists. Adult T-cell leukemia caused by HTLV-1 infection and AIDS caused by HIV-1 infection are the first human examples of such diseases. There are, however, numerous examples of retrovirus infection in non-human species. Because of the special threat that AIDS represents, many efforts have been and are being made to combat the spread of the disease and to cure individuals infected with HIV-1.

AZT represents the first FDA-approved drug for therapy of AIDS. In the laboratory, AZT was shown to inhibit the reverse transcriptase of HIV-1 and thereby prevent the replication of the virus in cultured cells. Unfortunately, its ability to prevent viral replication and subsequent pathogenic effects in the patient have been limited. Though efforts have been made to create other unique nucleoside analogs, none have been demonstrated to affect specifically the HIV-1 reverse transcriptase.

Several companies have attempted to create vaccines to prevent the spread of HIV-1. For an AIDS vaccine to be efficacious it must: (1) generate high levels of antibodies, (2) be capable of neutralizing HIV-1, (3) create cell-mediated immunity, and (4) be cross-reactive with different strains of HIV-1. On the basis of the vast accumulated experience with retroviruses of non-human animals, it is unlikely that a vaccine can be developed. Most animals infected with such viruses carry high-titer antibodies to the viruses and nonetheless remain viremic. In the case of AIDS, any vaccine against HIV-1 might be useful only for individuals who have never been exposed to HIV-1. Soluble CD4 protein is being developed as a possible therapeutic for the prevention of the spread of HIV-1 in infected patients. This therapy is based on the concept that soluble CD4 molecules will bind more effectively HIV-1 particles than will membrane CD4 receptor molecules, and thereby will prevent the spread of the virus into uninfected cells of the patient. This strategy has no precedent, and it is unclear if it will be successful.

In contrast to the above untried approaches, it should be possible to use ribozyme-based technology to treat HIV infection, and related diseases of white blood cells which are subject to transformation by retroviral vectors carrying targeted ribozymes. Particular examples of diseases that may be treated using targeted ribozymes include not only HTLV-1, but also various retroviral-induced leukemias. Other types of transformed tissues that might be treatable include intestinal and mammary cells carrying identified oncogenes of known sequence.

Modifications and variations of the methods and compositions using hepatitis delta ribozyme based technology will be obvious to those skilled in the art from the foregoing detailed description. Such modifications and variations are intended to come within the scope of the appended claims.

We claim:

1. A method for cleaving a target RNA molecule comprising:

mixing with the target RNA molecule a separate delta RNA fragment consisting of at least 18 consecutive nucleotides from the conserved region of the hepatitis delta virus, wherein the conserved region of the hepatitis delta RNA is selected from the group consisting of regions of hepatitis delta virus having ribozyme activity between residues 611 and 771 on the genomic strand and between residues 845 and 980 on the complementary anti-genomic strand, wherein the RNA fragment having ribozyme activity cleaves the target RNA molecule to form a 2',3' cyclic phosphate and 5' hydroxyl.

2. The method of claim 1 further comprising labelling the delta RNA fragment having ribozyme activity prior to mixing the fragment with the target RNA molecule.

3. The method of claim 2 further comprising screening isotropic cells with the labelled delta RNA fragment and detecting RNA molecules which form secondary and tertiary structure with the delta RNA fragment and are cleaved by the delta RNA fragment.

4. The method of claim 1 wherein the target RNA molecule is the genome of a RNA virus or an mRNA encoded by an RNA virus.

5. The method of claim 4 wherein the RNA virus is selected from the group consisting of HIV-1 and HTLV-1.

6. The method of claim 1 further comprising inserting the delta RNA fragment into a retroviral vector prior to mixing the fragment with the target RNA molecule.

7. The method of claim 1 wherein the RNA fragment with ribozyme activity forms regions of secondary structure with the target RNA molecule between 10 and 20 base pairs in length.

8. The method of claim 1 wherein the RNA fragment is selected from the group consisting of regions of hepatitis delta virus between residues 611 and 771 on the genomic strand and regions of hepatitis delta virus between residues 816 and 980 on the complementary anti-genomic strand.

9. The method of claim 8 wherein the RNA molecule with ribozyme activity forms local tertiary structure with the target RNA molecule that is structurally equivalent to the tertiary structure formed between residues 703 to 735 of hepatitis delta virus genomic strand.

* * * * *